(12) United States Patent
Tonge et al.

(10) Patent No.: US 7,687,547 B2
(45) Date of Patent: Mar. 30, 2010

(54) DIPHENYL ETHER ANTIMICROBIAL COMPOUNDS

(75) Inventors: Peter J. Tonge, Setauket, NY (US); Todd Sullivan, Winsted, CT (US); Francis Johnson, Setauket, NY (US)

(73) Assignee: Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/209,174

(22) Filed: Aug. 22, 2005

(65) Prior Publication Data

US 2006/0041025 A1 Feb. 23, 2006

Related U.S. Application Data

(60) Provisional application No. 60/603,803, filed on Aug. 23, 2004.

(51) Int. Cl.
*A61K 31/075* (2006.01)
*C07C 43/23* (2006.01)

(52) U.S. Cl. ...................... 514/721; 568/638
(58) Field of Classification Search ............... 568/638, 568/721
See application file for complete search history.

(56) References Cited

U.S. PATENT DOCUMENTS

| 6,790,868 B2 * | 9/2004 | Harper et al. ............ 514/718 |
| 6,838,583 B2 | 1/2005 | Harper et al. |
| 7,211,700 B2 | 5/2007 | Harper et al. |
| 2005/0037925 A1 * | 2/2005 | Tsukamoto et al. ......... 504/238 |

FOREIGN PATENT DOCUMENTS

WO WO 2003016286 * 2/2003

OTHER PUBLICATIONS

Sivaraman et al., J. Med. Chem., Jan. 2004, vol. 47, pp. 509-518.*
Ungnade et al., Methoxy (and Hydroxy) Phenoxybenozoic Acids, Journal of Organic Chemisry, vol. 16, No. 8, Aug. 1951, pp. 1311-1317.*
Parham et al., 2,4-Dimethyldibenzofuran, The Journal of Organic Chemistry, vol. 26, No. 11, Nov. 1961, pp. 4749-4753.*
Richard B. Silverman, The Organic Chemistry of Drug Design and Drug Action, 1992, pp. 15-20.*
"Triclosan" Wikipedia. 2005. http://en.wikipedia.org/wiki/Triclosan.
Marcoux et al. (Oct. 1997) *J. Am. Chem. Soc.* 119:10539-10549.
Fu et al. (2002) *Angew. Chem. Int. Ed.* 41:4176-4211.
Neumeyer et al. (1990) *J. Med. Chem.* 33:521-526.
Author: Richard R. Silverman, Title: "The Organic Chemistry of Drug Design and Drug Action;" Publication: *Academic Press, Inc.* © 2004, pp. 17, 18, 29-34, 51-53, 57, 58, 68, 72 and 73.
Author: Erdal et al., Title: "Hydroxyethylene isosteres of selective neuronal nitric oxide synthase inhibitors;" Publication: *Bioorg. Med. Chem.* 15:6096-6108; Date of Publication: (2007).
Author: Jacobson et al., Title: "Structural Determinants of 4-Chloro-m-cresol Required for Activation of Ryanodine Receptor Type 1;" Publication: *Molecular Pharmacology* 70(1): 259-266; Date of Publication: (2006).
Author: Fujita, et al., Title: "A New Substituent Constant, π, Derived from Partition Coefficients;" Publication: *J. AmChem. Soc.*, 86:5175-80; Date of Publication: (1964).

* cited by examiner

*Primary Examiner*—Rosalynd Keys
(74) *Attorney, Agent, or Firm*—Hoffmann & Baron, LLP

(57) ABSTRACT

The present invention is directed to compounds having the formula:

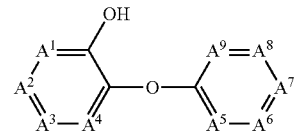

In the formula, $A^2$ represents N or $C-X^1_a-R^1$ and $A^4$ represents N or $C-X^2_b-R^2$, provided that $A^2$ and $A^4$ are not both N. $R^1$ and $R^2$ independently represent H or a hydrocarbon group, provided that $R^1$ and $R^2$ are not both H. The hydrocarbon groups of $R^1$ and $R^2$ are preferably alkyl or alkenyl groups. More preferably, the hydrocarbon groups are alkyl groups. $A^1$, $A^3$, $A^6$, and $A^8$ independently represent CH or N. $A^5$ and $A^9$ independently represent $CR^3$ or N, wherein $R^3$ independently represents H, methyl, ethyl, or halo. $A^7$ represents $CR^4$ or N, wherein $R^4$ represents H, methyl, ethyl, halo, nitro, hydroxy, amino, amido, or a methyl or ethyl group substituted independently with halo, nitro, hydroxy, amino, or amido. Not more than three of $A^5$, $A^6$, $A^7$, $A^8$, and $A^9$ are N.

24 Claims, No Drawings

DIPHENYL ETHER ANTIMICROBIAL COMPOUNDS

This application asserts priority to U.S. Provisional Application Ser. No. 60/603,803, filed on Aug. 23, 2004. The specification of U.S. Provisional Application Ser. No. 60/603,803 is hereby incorporated by reference in its entirety.

The present invention was made with government support under Grant No. 2R21AI04463905 awarded by the National Institutes of Health. The United States government has certain rights in this invention.

BACKGROUND OF THE INVENTION

It is known that many antimicrobial drugs are becoming less effective against increasingly virulent and drug-resistant organisms. Hence, the benefits of new, more effective antimicrobial agents are well recognized.

Triclosan, (2,4,4'-trichloro-2'-hydroxydiphenyl ether), has been widely used for more than thirty years as an antibacterial agent in numerous consumer products, including toothpastes, mouthwashes, soaps, children's toys, and kitchen equipment. The widespread use of triclosan was predicated on the belief that triclosan acts through a non-specific mechanism involving bacterial membrane disruption. Triclosan was, therefore, assumed not to induce resistant strains of bacteria.

Recent findings, however, show that triclosan does not act non-specifically as originally thought, but rather, specifically, by inhibiting the fatty acid biosynthesis (FAS) pathway in certain bacteria and other organisms. In particular, it has been found that in numerous organisms, including *Escherichia coli, Staphylococcus aureus, Bacillus subtilis*, and the malarial parasite *Plasmodium falciparum*, triclosan targets an NADH-dependent trans-2-enoyl-ACP reductase known as FabI. The foregoing organisms are believed to overcome the action of triclosan by mutating the gene that encodes FabI, also known as the fabI gene. Not surprisingly, then, it has also been found that triclosan is not immune to resistance, and that, in fact, bacteria are becoming increasingly triclosan-resistant.

A notable example of anti-bacterial resistance is found in the case of tuberculosis. Tuberculosis is a debilitating disease responsible for the deaths of three million people per year. Isoniazid, also known as isonicotinic acid hydrazide, or INH, is currently the most relied upon drug for the treatment of tuberculosis. Due to the increasing prevalence of resistance in *Mycobacterium tuberculosis*, current tuberculosis treatment regimens typically include the use of multiple antibiotics over an extended period of time. A typical regimen for treating tuberculosis is the administration of isoniazid, rifampicin, and pyrazinamide in combination with ethanbutol or streptomycin for two months, followed by the administration of isoniazid and rifampicin for four months.

Such multiple drug treatments, even if effective, have significant disadvantages, such as increased risk of side-effects by patients, prolonged treatment time, and high expense. In addition, multiple drug treatment is being severely compromised by the emergence of multi-drug resistant *M. tuberculosis* (MDR-TB).

As with triclosan, isoniazid targets the fatty acid synthase pathway of *M. tuberculosis*. In order to be effective, isoniazid requires activation by the mycobacterial catalase-peroxidase enzyme KatG.

At least one mode by which *M. tuberculosis* resists isoniazid is a genetic mutation of the KatG enzyme. The alteration of the KatG enzyme disables the activation of isoniazid, thereby significantly reducing the efficacy of the drug.

The diazaborines are another class of compounds known to target FabI in *E. Coli*. The diazaborines form a covalent adduct with the NAD(H) cofactor. Diazaborine-resistant organisms arise from genetic mutations that alter the residues that form the NAD-diazaborine binding pocket, thereby reducing the affinity of the drug for the enzyme.

Accordingly, there is a need for new and improved antimicrobial compounds that are effective against increasingly virulent and drug-resistant organisms, and that overcome the limitations of the drugs described thus far.

SUMMARY OF THE INVENTION

These, and other objectives as will be apparent to those of ordinary skill in the art, have been achieved by providing a compound having the formula:

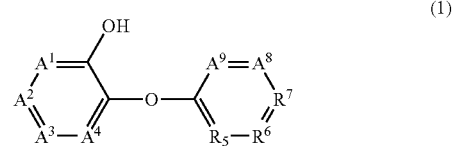

(1)

wherein $A^1$, $A^3$, $A^6$, and $A^8$ independently represent CH or N;

$A^2$ represents N or C—$X^1_a$—$R^1$;

$A^4$ represents N or C—$X^2_b$—$R^2$;

$R^1$ and $R^2$ independently represent H, or a hydrocarbon containing a minimum of one carbon atom and a maximum of twenty six carbon atoms, wherein the hydrocarbon is unsubstituted, or is substituted with one or more of —OH, —$NH_2$, —SH, halo, or —COOH;

$X^1$ and $X^2$ independently represent —O—, —S—, —NH—, —C(O)O—, —C(O)—, —C(O)NH—, or —$SO_2$NH—;

a and b independently represent 0 or 1, provided that when a and b are both 0, then $R^1$ and $R^2$ are not both H; when a is 1, then $R^1$ is not H; and when b is 1, then $R^2$ is not H;

$A^5$ and $A^9$ independently represent $CR^3$ or N;

$R^3$ represents H, methyl, ethyl, or halo;

$A^7$ represents $CR^4$ or N;

$R^4$ represents H, methyl, ethyl, halo, nitro, hydroxy, amino, amido, or a methyl or an ethyl group substituted with halo, nitro, hydroxy, amino, or amido;

provided that $A^2$ and $A^4$ are not both N; and not more than three of $A^5$, $A^6$, $A^7$, $A^8$, and $A^9$ are N.

The invention is further directed to a method of inhibiting in a mammal in need thereof the growth of a bacterium containing an enoyl reductase enzyme encoded by a fabI gene, a fabK gene, a fabL gene, or a combination thereof. The method comprises administering to the mammal an effective amount of a compound according to the invention.

Still further, the invention is directed to a pharmaceutical composition for inhibiting the growth of a bacterium containing an enoyl reductase enzyme encoded by a fabI gene, a fabK gene, a fabL gene, or a combination thereof. The composition comprises a compound of the invention and a pharmaceutically acceptable carrier.

DETAILED DESCRIPTION OF THE INVENTION

In one embodiment, the invention relates to a compound having the formula:

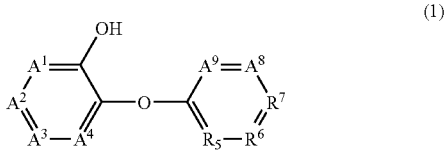

(1)

In the formula, $A^2$ represents N or C—$X^1_a$—$R^1$ and $A^4$ represents N or C—$X^2_b$—$R^2$, provided that $A^2$ and $A^4$ are not both N. $R^1$ and $R^2$ may independently represent H or a hydrocarbon group, provided that $R^1$ and $R^2$ are not both H. The hydrocarbon groups of $R^1$ and $R^2$ are preferably alkyl or alkenyl groups. More preferably, the hydrocarbon groups are alkyl groups.

The hydrocarbon group contains a minimum of one carbon atom. Preferably, the hydrocarbon group contains a minimum of three carbon atoms. More preferably, the hydrocarbon group contains a minimum of four carbon atoms.

The hydrocarbon group contains a maximum of twenty six carbon atoms. Preferably, the hydrocarbon group contains a maximum of eighteen carbon atoms. More preferably, the hydrocarbon group contains a maximum of twelve carbon atoms. Even more preferably, the hydrocarbon group contains a maximum of eight carbon atoms.

The hydrocarbon group may be saturated or unsaturated; straight-chained, branched, or cyclic. An unsaturated hydrocarbon group contains one or more double or triple bonds.

Saturated hydrocarbon groups include, for example, alkyl and cycloalkyl groups. Some examples of straight-chained alkyl groups include methyl, ethyl, propyl, butyl, pentyl, hexyl, octyl, decyl, dodecyl, hexadecyl, eicosyl, docosyl, and hexacosyl. Some examples of branched alkyl groups include iso-propyl, iso-butyl, sec-butyl, t-butyl, di-(t-butyl)methyl, 3-ethyl-2,3-dimethylhexyl, and 4-(1,1-dimethylethyl)heptyl. Some examples of cycloalkyl groups include cyclopropyl, cyclobutyl, cyclopentyl, cyclohexyl, and cycloheptyl.

Unsaturated hydrocarbon groups include, for example, alkenyl, alkynyl, cycloalkenyl, aryl, heteroaryl, and combination groups thereof. Some examples of alkenyl groups include vinyl, allyl, 2-butenyl, 3-butenyl, 2-methylene-3-butenyl, 9-decylenyl, oleyl, linolenyl, palmitoleyl, and arachidonyl. Some examples of cycloalkenyl groups include cyclobutenyl, cyclopentenyl, cyclohexenyl, cyclohexa-1,3-dienyl, and bicyclo[4.4.0]decenyl. Some examples of alkynyl groups include acetylenyl, propargyl, and butynyl.

A preferred aryl group is phenyl. Some examples of heteroaryl groups include pyridinyl, pyrimidinyl, triazinyl, imidazolyl, benzimidazolyl, pyrrolyl, furyl, thiophenyl, oxazolyl, and thiazolyl.

Any of the rings mentioned above, such as cycloalkyl, cycloalkenyl, aryl, and heteroaryl rings, may be fused to other cycloalkyl, cycloalkenyl, aryl, and heteroaryl rings. Some examples of cycloalkyl rings fused to other cycloalkyl rings include decalinyl, bicyclo[3.3.0]octanyl, and bicyclo[4.2.0]octanyl rings. Some examples of cycloalkyl rings fused to aryl rings include bicyclo[4.3.0]nonenyl, bicyclo[4.4.0]decenyl, and bicyclo[4.4.0]dec-7,9-dienyl rings. Some examples of aryl rings fused to other aryl rings include naphthyl, phenanthryl, anthracenyl, triphenylenyl, and chrysenyl rings. Some examples of heteroaryl rings fused to aryl rings include cinnolinyl, phthalazinyl, and quinazolinyl rings. Some examples of heteroaryl rings fused to other heteroaryl rings include purinyl, 2,6-naphthyridinyl, and 1,8-naphthyridinyl rings.

Any of the hydrocarbon groups described above may be either unsubstituted, or substituted with one or more —OH, —$NH_2$, —SH, halo, or —COOH groups. Halo includes, for example, F, Cl, and Br. Some examples of substituted hydrocarbon groups include amino acids, fatty acids, 2-hydroxyethyl, 2-aminoethyl, 2-mercaptoethyl, trifluoromethyl, chlorobutyl, 4-bromobenzyl, 4-hydroxycyclohexyl, p-hydroxyphenyl, 2,6-dimethyl-4-hydroxyphenyl, and 2,6-dihydroxy-4-(t-butyl)benzyl.

The hydrocarbon groups of $R^1$ and $R^2$ can also be saturated or unsaturated rings substituted with any of the hydrocarbon groups thus far described. For example, the hydrocarbon group can be a saturated or unsaturated ring substituted with one or more straight-chained or branched alkyl or alkenyl groups. The maximum total number of carbon atoms in these hydrocarbon-substituted rings is twenty six.

Some examples of alkyl-substituted cycloalkyl groups include 2-methylcyclopentyl, 2,6-dimethylcyclohexyl, and 4-(t-butyl)cyclohexyl. Some examples of alkenyl-substituted cycloalky groups include vinylcyclohexyl and allylcyclopentyl. An example of a cycloalkyl-substituted cycloalkyl group includes bicyclohexyl. Similarly, some examples of hydrocarbon-substituted cycloalkenyl groups include 3,4-dimethyl-3-cyclopentenyl, 4-vinyl-1-cyclohexenyl, and 1,1-bi-cyclopentenyl.

Some examples of alkyl-substituted aryl groups include tolyl, mesityl, xylyl, cumenyl, cymenyl, 3,5-di(t-butyl)phenyl, and 2-methylnaphthyl. Some examples of alkenyl-substituted aryl groups include 2-vinylphenyl, 2-vinylbenzyl, and 2-vinylnaphthyl. An example of a cycloalkyl-substituted aryl group includes cyclohexylphenyl. Some examples of aryl-substituted aryl groups include biphenyl and p-terphenyl.

Similarly, some examples of hydrocarbon-substituted heteroaryl groups include 2-methylpyridinyl, 2-ethylpyridinyl, 1-vinylimidazolyl, 2-methylquinoxalinyl, 1-allylbenzotriazolyl, 2,2'-bipyridyl, and 4-methyl-2,6-naphthyridinyl.

$X^1$ and $X^2$ in formula (1) are optional linkers. $X^1$ and $X^2$ are preferably independently represented by —O—, —S—, —NH—, —C(O)O—, —C(O)—, —C(O)NH—, or —$SO_2$NH—. The —C(O)O—, —C(O)—, —C(O)NH—, and —$SO_2$NH— linkers are bound in either of two possible orientations. For example, —C(O)O— also includes —OC(O)—; —C(O)NH— also includes —NHC(O)—; and —$SO_2$NH— also includes —NH$SO_2$—.

In C—$X^1_a$—$R^1$ and C—$X^2_b$—$R^2$ in formula (1), a and b independently represent 0 or 1. When a is zero, then $R^1$ is directly bound to C, and when b is zero, then $R^2$ is directly bound to C. When a and b are both 0, then $R^1$ and $R^2$ are both directly bound to C and $R^1$ and $R^2$ are not both H.

When a is 1, $R^1$ is bound indirectly to C through $X^1$. Likewise, when b is 1, $R^2$ is bound indirectly to C through $X^2$. When a is 1, then $R^1$ is not H, and when b is 1, then $R^2$ is not H.

In formula (1), $A^1$, $A^3$, $A^6$, and $A^8$ independently represent CH or N. $A^5$ and $A^9$ independently represent $CR^3$ or N, wherein $R^3$ independently represents H, methyl, ethyl, or halo. $A^7$ represents $CR^4$ or N, wherein $R^4$ represents H, methyl, ethyl, halo, nitro, hydroxy, amino, amido, or a methyl or ethyl group substituted independently with halo, nitro, hydroxy, amino, or amido. Not more than three of $A^5$, $A^6$, $A^7$, $A^8$, and $A^9$ are N.

In a preferred embodiment, $A^2$ represents $C(X^1)_a$—$R^1$ and $A^4$ represents $C(X^2)_b$—$R^2$. More preferably, a and b are both 0, and either $R^1$ or $R^2$ is H. Even more preferably, $R^2$ is H and $R^1$ is a hydrocarbon containing a minimum of one carbon atom and a maximum of twenty six carbon atoms.

In a first embodiment, the compound is a 2-hydroxy-3-phenoxypyridine derivative, wherein $A^1$ represents N; $A^2$ represents $CR^1$, and $A^3$, $A^4$, $A^5$, $A^6$, $A^7$, $A^8$ and $A^9$ represent CH. In a second embodiment, the compound is a 2-(pyridin-4-yloxy)phenol derivative, wherein $A^1$, $A^3$, $A^4$, $A^5$, $A^6$, $A^8$ and $A^9$ represent CH; $A^2$ represents $CR^1$, and $A^7$ represents N. In a third embodiment, the compound is a 2-phenoxy-3-hydroxypyridine derivative, wherein $A^1$, $A^3$, $A^5$, $A^6$, $A^7$, $A^8$ and $A^9$ represent CH; $A^2$ represents $CR^1$; and $A^4$ represents N. In a fourth embodiment, the compound is a 3-(pyridin-4-yloxy)pyridin-2-ol derivative, wherein $A^1$ and $A^7$ represent N; $A^2$ represents $CR^1$; and $A^3$, $A^4$, $A^5$, $A^6$, $A^8$ and $A^9$ represent CH.

Preferably, $A^1$ represents CH, $A^3$ represents CH, $A^5$ represents $CR^3$, wherein $R^3$ represents H, $A^6$ represents CH, $A^7$ represents $CR^4$, wherein $R^4$ represents H, $A^8$ represents CH, and $A^9$ represents $CR^3$, wherein $R^3$ represents H.

More preferably, the compounds of the invention are represented by the formulas:

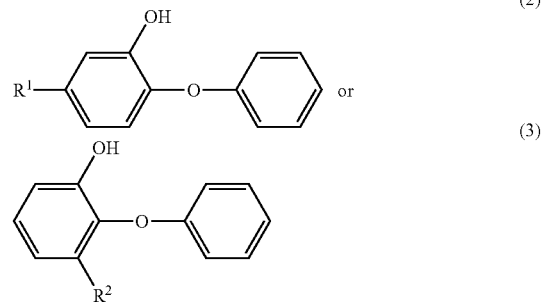

In formulas (2) and (3), $R^1$ and $R^2$ have the meaning described above. More preferably, $R^1$ and $R^2$ are straight-chained alkyl groups containing a minimum of four carbon atoms and a maximum of twenty six carbon atoms. The following table lists some additional exemplary compounds of the invention.

TABLE 1

Exemplary compounds of the invention

| No. | Name of compound | A1 | A2 | A3 | A4 | A5 | A6 | A7 | A8 | A9 |
|---|---|---|---|---|---|---|---|---|---|---|
| 1 | 5-ethyl-2-phenoxyphenol | CH | C—$C_2H_5$ | CH | CH | CH | CH | CH | CH | CH |
| 2 | 2-phenoxy-5-propylphenol | CH | C-(n-$C_3H_7$) | CH | CH | CH | CH | CH | CH | CH |
| 3 | 5-isopropyl-2-phenoxyphenol | CH | C-(i-$C_3H_7$) | CH | CH | CH | CH | CH | CH | CH |
| 4 | 5-butyl-2-phenoxyphenol | CH | C-(n-$C_4H_9$) | CH | CH | CH | CH | CH | CH | CH |
| 5 | 2-phenoxy-5-(t-butyl)phenol | CH | C-(t-$C_4H_9$) | CH | CH | CH | CH | CH | CH | CH |
| 6 | 5-pentyl-2-phenoxyphenol | CH | C-(n-$C_5H_{11}$) | CH | CH | CH | CH | CH | CH | CH |
| 7 | 5-hexyl-2-phenoxyphenol (5a) | CH | C-(n-$C_6H_{13}$) | CH | CH | CH | CH | CH | CH | CH |
| 8 | 5-octyl-2-phenoxyphenol (5b) | CH | C-(n-$C_8H_{17}$) | CH | CH | CH | CH | CH | CH | CH |
| 9 | 5-decyl-2-phenoxyphenol | CH | C-(n-$C_{10}H_{21}$) | CH | CH | CH | CH | CH | CH | CH |
| 10 | 5-dodecyl-2-phenoxyphenol | CH | C-(n-$C_{12}H_{25}$) | CH | CH | CH | CH | CH | CH | CH |
| 11 | 5-hexadecyl-2-phenoxyphenol | CH | C-(n-$C_{16}H_{33}$) | CH | CH | CH | CH | CH | CH | CH |
| 12 | 2-phenoxy-5-tetracosylphenol | CH | C-(n-$C_{24}H_{49}$) | CH | CH | CH | CH | CH | CH | CH |
| 13 | 5-butyl-2-(2-methylphenoxy)phenol | CH | C-(n-$C_4H_9$) | CH | CH | CH | CH | CH | CH | C—$CH_3$ |
| 14 | 5-butyl-2-(2-ethylphenoxy)phenol | CH | C-(n-$C_4H_9$) | CH | CH | CH | CH | CH | CH | C—$C_2H_5$ |
| 15 | 2-(2,6-dimethylphenoxy)-5-butyl-phenol | CH | C-(n-$C_4H_9$) | CH | CH | C—$CH_3$ | CH | CH | CH | C—$CH_3$ |
| 16 | 2-(2-chlorophenoxy)-5-pentyl-phenol | CH | C-(n-$C_5H_{11}$) | CH | CH | CH | CH | CH | CH | C—Cl |
| 17 | 2-(4-nitrophenoxy)-5-pentyl-phenol | CH | C-(n-$C_5H_{11}$) | CH | CH | CH | CH | C—$NO_2$ | CH | CH |
| 18 | 2-(4-hydroxyphenoxy)-5-pentyl-phenol | CH | C-(n-$C_5H_{11}$) | CH | CH | CH | CH | C—OH | CH | CH |
| 19 | 2-(4-methylphenoxy)-5-pentyl-phenol | CH | C-(n-$C_5H_{11}$) | CH | CH | CH | CH | C—$CH_3$ | CH | CH |
| 20 | 2-(4-chlorophenoxy)-5-pentyl-phenol | CH | C-(n-$C_5H_{11}$) | CH | CH | CH | CH | C—Cl | CH | CH |
| 21 | 3-ethyl-2-phenoxyphenol | CH | CH | CH | C—$C_2H_5$ | CH | CH | CH | CH | CH |
| 22 | 3-hexyl-2-phenoxyphenol | CH | CH | CH | C-(n-$C_6H_{13}$) | CH | CH | CH | CH | CH |
| 23 | 3-octyl-2-phenoxyphenol | CH | CH | CH | C-(n-$C_8H_{15}$) | CH | CH | CH | CH | CH |
| 24 | 3-dodecyl-2-phenoxyphenol | CH | CH | CH | C-(n-$C_{12}H_{25}$) | CH | CH | CH | CH | CH |
| 25 | 3,5-dimethyl-2-phenoxyphenol | CH | C—$CH_3$ | CH | C—$CH_3$ | CH | CH | CH | CH | CH |
| 26 | 5-ethyl-3-hexyl-2-phenoxyphenol | CH | C—$C_2H_5$ | CH | C-(n-$C_6H_{13}$) | CH | CH | CH | CH | CH |
| 27 | 3-hexyl-2-(2-fluorophenoxy)phenol | CH | CH | CH | C-(n-$C_6H_{13}$) | CH | CH | CH | CH | C—F |
| 28 | 3-decyl-2-(2-trifluoromethylphenoxy)phenol | CH | CH | CH | C-(n-$C_{10}H_{21}$) | CH | CH | CH | CH | C—$CF_3$ |
| 29 | 6-ethyl-2-hydroxyl-3-phenoxypyridine | N | C—$C_2H_5$ | CH | CH | CH | CH | CH | CH | CH |
| 30 | 3-hydroxy-5-octyl-2-phenoxypyridine | CH | C-(n-$C_8H_{17}$) | CH | N | CH | CH | CH | CH | CH |
| 31 | 3-hydroxy-5-octyl-4-phenoxypyridine | CH | N | CH | C-(n-$C_8H_{17}$) | CH | CH | CH | CH | CH |
| 32 | 2-hydroxy-6-octyl-3-phenoxypyrazine | N | C-(n-$C_8H_{17}$) | CH | N | CH | CH | CH | CH | CH |
| 33 | 5-octyl-2-(pyridin-4-yloxy)phenol | CH | C-(n-$C_8H_{17}$) | CH | CH | CH | CH | N | CH | CH |
| 34 | 2-hydroxy-6-octyl-3-(pyridin-4-yloxy)pyridine | N | C-(n-$C_8H_{17}$) | CH | CH | CH | CH | N | CH | CH |
| 35 | 2-hydroxy-6-octyl-3-(pyridin-4-yloxy)pyrazine | N | C-(n-$C_8H_{17}$) | CH | N | CH | CH | N | CH | CH |
| 36 | 5-octyl-2-(pyrimidin-4-yloxy)phenol | CH | C-(n-$C_8H_{17}$) | CH | CH | CH | CH | N | CH | N |
| 37 | 5-octyl-2-([1,3,5]triazin-2-yloxy)-phenol | CH | C-(n-$C_8H_{17}$) | CH | CH | N | CH | N | CH | N |
| 38 | 3-hydroxy-5-octyl-2-(pyrimidin-4-yloxy)pyridine | CH | C-(n-$C_8H_{17}$) | CH | N | CH | CH | N | CH | N |
| 39 | 3-hydroxy-5-octyl-2-(2-methylpyrimidin-4-yloxy)pyridine | CH | C-(n-$C_8H_{17}$) | CH | N | CH | CH | N | C—$CH_3$ | N |
| 40 | 3-hydroxy-5-octyl-4-(2-methylpyrimidin-4-yloxy)pyridine | CH | N | CH | C-(n-$C_8H_{17}$) | CH | CH | N | C—$CH_3$ | N |
| 41 | 6-ethyl-4-hydroxy-3-phenoxypyridine | CH | C—$C_2H_5$ | N | CH | CH | CH | CH | CH | CH |
| 42 | 2-ethyl-4-hydroxy-5-phenoxypyrimidine | N | C—$C_2H_5$ | N | CH | CH | CH | CH | CH | CH |
| 43 | 2,6-dimethyl-4-hydroxy-5-phenoxypyrimidine | N | C—$CH_3$ | N | C—$CH_3$ | CH | CH | CH | CH | CH |

The compounds of the invention are directed to inhibiting the growth of microbes, and in particular, bacteria. For example, the compounds of the invention are effective in inhibiting the growth of bacteria such as M. tuberculosis, E. coli, Staphylococcus aureus, Haemophilus influenza, Salmonella enterica, Salmonella typhimurium, Bordetella pertussis, Neisseria meningitides, Neisseria gonorrhoeae, Legionella pneumophila, Bacillus anthracis, Yersinia pestis, Streptococcus pneumoniae, Enterococcus faecalis, and Bacillus subtilis. The compounds of the invention are particularly effective in inhibiting the growth of E. coli and certain species in the genus of mycobacteria, such as M. tuberculosis and M. leprae.

Without being bound by any theory, it is believed that the compounds of the invention inhibit the growth of bacteria by inhibiting a component involved in bacterial fatty acid biosynthesis. In particular, it is believed that the compounds of the invention inhibit bacterial fatty acid biosynthesis by inhibiting enoyl reductase enzymes.

Bacterial enoyl reductase enzymes are encoded by certain genes, e.g., the fabI gene, the fabK gene, and the fabL gene. The enoyl reductase enzymes are named according to the gene encoding them. Thus, the corresponding enoyl reductase enzymes are commonly referred to as FabI, FabK, and FabL reductases, respectively. In addition, several structurally related, but distinct, species may belong to each of the FabI, FabK, and FabL reductases. For example, the enoyl reductase enzyme InhA in M. tuberculosis belongs to the FabI class of reductases.

In a further embodiment, the invention relates to a method of inhibiting the growth of a bacterium containing an enoyl reductase enzyme encoded by a fabI gene, a fabK gene, a fabL gene, or a combination thereof, in a mammal in need thereof. The method comprises administering to the mammal an effective amount of a compound of the invention.

The growth inhibition of microbes according to the invention is not limited to any mechanism. It is interesting to note, however, that in E. coli, the compounds of the invention are believed to target a FabI reductase. In M. tuberculosis, the compounds of the invention are believed to target InhA, a species in the class of FabI reductases, or KasA, one of three ketoacyl synthases in the FAS II pathway, or a combination thereof.

In one embodiment, the compounds of the invention inhibit M. tuberculosis by targeting InhA or KasA directly, without requiring an activation step. The activation is believed to be mediated by a mycobacterial catalase-peroxidase enzyme, such as KatG. It has been found that at least one mode by which the efficacy of currently known drugs is resisted by M. tuberculosis is the occurrence of one or more genetic mutations of the katg gene that encodes the KatG enzyme. The mutation(s) disable the activation of the drug. Thus, those compounds that can inhibit the growth of M. tuberculosis without requiring an activation step are significantly advantageous. A further advantage of such compounds of the invention against M. tuberculosis is that the compounds inhibit the growth of multi-drug resistant M. tuberculosis.

In another embodiment, the invention relates to a method of inhibiting the growth of a plasmodium in a mammal in need thereof. The plasmodium contains an enoyl reductase enzyme. In one embodiment, the invention is directed to inhibiting the growth of Plasmodium falciparum. The method comprises administering to the mammal an effective amount of a compound according to the invention. Preferably, the compound has formula (2) or (3).

The compounds of the invention may be administered by any method known in the art. Some examples of suitable modes of administration include oral, intravenous, intramuscular, topical or any other parenteral mode of administration. The compounds of the invention may be administered alone or in combination with other conventional drugs, such as other drugs for inhibiting the growth of microbes containing an enoyl reductase enzyme.

The compounds can be administered orally by any method known in the art. Liquid or solid oral formulations may be used. Some examples of formulations suitable for oral administration include tablets, capsules, pills, troches, elixirs, suspensions, and syrups.

The administration can be intranasal, in the form of, for example, a nebulizer, liquid mist, or intranasal spray; or transdermal, in the form of, for example, a patch; or rectal, in the form of, for example, a suppository; or intrabronchial, in the form of, for example, an inhaler spray.

The timing of the administration of the pharmaceutical composition may also be regulated. For example, the compounds may be administered intermittently or by controlled release. Controlled release administration is a method of drug delivery that achieves at least a minimally effective level of the drug over a specified period of time. The level typically is measured by serum concentration.

In another embodiment, the invention is directed to a pharmaceutical composition comprising a compound according to formula (1) and a pharmaceutically acceptable carrier. In a preferred embodiment, the pharmaceutical composition comprises a compound according to formula (2) or (3).

The compounds are either uncharged or in the form of pharmaceutically acceptable salts. The term "pharmaceutically acceptable salt" refers to a salt prepared from a suitable compound and, for example, an acid or a base. The salt is acceptably non-toxic and has acceptable pharmacokinetics. Such salts are formed by well known procedures.

Suitable acids for producing salts of the compounds of the invention include mineral acids and organic acids. Some examples of mineral acids include hydrochloric, hydriodic, hydrobromic, phosphoric, metaphosphoric, nitric and sulfuric acids. Some examples of organic acids include tartaric, acetic, citric, maleic, malic, benzoic, glycollic, gluconic, gulonic, succinic, arenesulfonic, e.g. p-toluenesulfonic acids, and the like.

Suitable bases for producing salts of the compounds of the invention include inorganic bases and organic bases. Some examples of inorganic bases include ammonia and the hydroxides of lithium, sodium, potassium, magnesium and calcium. Some examples of organic bases include primary, secondary, and tertiary alkyl amines.

In this specification, a pharmaceutically acceptable carrier is considered to be synonymous with a vehicle or an excipient as understood by practitioners in the art. Examples of carriers include starch, milk, sugar, certain types of clay, gelatin, stearic acid or salts thereof, magnesium or calcium stearate, talc, vegetable fats or oils, gums and glycols.

The compounds of the inventions may also include one or more of the following: a stabilizer, a surfactant, preferably a nonionic surfactant, and optionally a salt and/or a buffering agent.

The stabilizer may be, for example, an amino acid, such as glycine; or an oligosaccharide, such as sucrose, tetralose, lactose or a dextran. Alternatively, the stabilizer may be a sugar alcohol, such as mannitol; or any suitable combination thereof.

The surfactant may be, for example, an ionic surfactant such as a polyacrylate. Alternatively, the surfactant may be a nonionic surfactant, such as a polysorbate. Some other examples of non-ionic surfactants include polyethylene glycol and polypropylene glycol.

The salt or buffering agent may be any suitable salt or buffering agent, such as, for example, sodium chloride, or a sodium or potassium phosphate, respectively. The salt and/or buffering agents are useful for maintaining the osmolality at a level suitable for administration to a mammal, and for maintaining the pH of the compounds of the invention.

The compounds of the inventions may additionally contain one or more conventional additives. Some examples of such additives include a solubilizer, such as, for example, glycerol; an antioxidant such as, for example, benzalkonium chloride (a mixture of quaternary ammonium compounds, known as "quart"), benzyl alcohol, chloretone or chlorobutanol; an anaesthetic agent such as, for example, a morphine derivative; or an isotonic agent, etc. As a further precaution against oxidation or other spoilage, the compounds of the inventions may be stored under nitrogen gas in vials sealed with impermeable stoppers.

When aqueous suspensions are used for oral administration, emulsifying and/or suspending agents are commonly added. In addition, coloring, sweetening and/or flavoring agents may be added to the oral compositions.

Pharmaceutical compositions are preferably sterile. In addition, for intravenous use, the total concentration of the solute(s) can be controlled in order to render the preparation isotonic.

Carrier compositions deemed to be suited for topical use include gels, salves, lotions, creams, ointments and the like. The compounds can also be incorporated within a support base or matrix, or the like, which can be directly applied to skin.

Any mammal in need thereof can be treated in accordance with the present invention. Mammals include, for example, humans, baboons, and other primates, as well as pet animals such as dogs and cats, laboratory animals such as rats and mice, and farm animals such as horses, sheep, and cows.

An "effective amount" of a compound of the invention is an administered amount which effectively treats a disease or condition by inhibiting the growth of microbes in a mammal needing such treatment. An effective amount includes a minimally effective concentration for inhibiting the growth of microbes in a mammal. The amount required for effective treatment is governed by pharmacological standards and by the discretion of medical practitioners in the art.

The effective amount of a compound of the invention is determined during clinical trials as known in the art. Examples of effective amounts include, for example, 10-1000 mg per day of the compound.

The compounds of the present invention are synthesized according to methods known in the art. Of particular synthetic value are Buchwald's carbon-oxygen cross-coupling and Negishi's carbon-carbon cross-coupling methods. See Marcoux, J. F., Doye, S., Buchwald, S. L. (1997) J. Am. Chem. Soc 119, 10539-10540; Fu, G. C., Littke, A. F. (2002) Angew. Chem. Int. Ed. 41, 4176-4211; and Neumeyer, J., Baindur, N., Yuan, J., Booth, G., Seeman, P., Niznik, H. B. (1990) J. Med. Chem. 33, 521-526. Shown below for the purpose of illustration is a method for synthesizing some exemplary compounds of the invention.

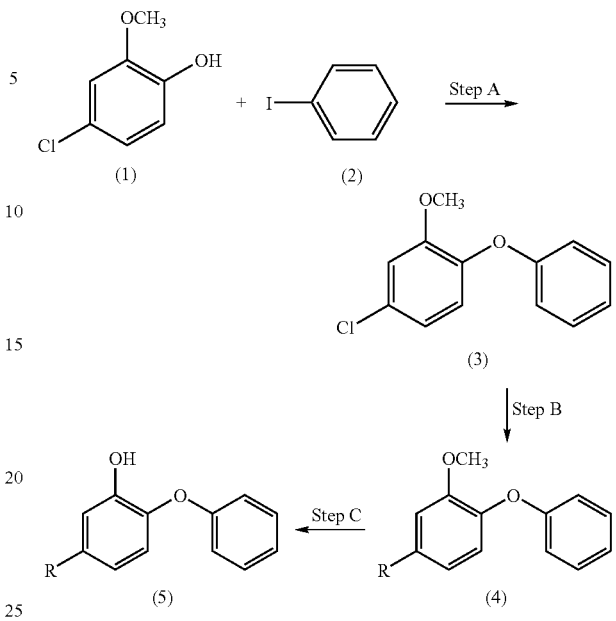

In Step A, the formation of the carbon-oxygen bond is generated by the coupling of the phenol (1) with an aryl halide such as (2) using a copper complex in toluene to form compound (3). In Step B, the formation of the carbon-carbon bond between the aryl ring and R is achieved by the use of carbon-carbon coupling methods known in the art, such as by a palladium catalyst and a Grignard reagent to form compound (4), where R is a hydrocarbon. The final product (5) is generated in Step C by the use of an ether-cleaving reagent, such as $BBr_3$ or $AlCl_3$.

Examples have been set forth below for the purpose of illustration and to describe the best mode of the invention at the present time. However, the scope of this invention is not to be in any way limited by the examples set forth herein.

Example 1

Reaction Step A: Synthesis of 4-chloro-2-methoxy-1-phenoxybenzene (3)

Iodobenzene (7.35 mmol), 4-chloro-2-methoxyphenol (14.7 mmol), $Cs_2CO_3$ (32.3 mmol), copper(I) trifluoromethanesulfonate benzene complex (0.735 mmol, 5.0 mol % Cu), ethyl acetate (0.125 mmol, 5.0 mol %), 1-naphthoic acid (32.3 mmol), molecular sieves 4A (1.8 g) and toluene (15 mL) were added to an oven-dried 50 mL two-necked round-bottomed flask. The flask was sealed with a rubber septum, purged with nitrogen, and the temperature raised to 110° C. overnight and monitored by thin layer chromatography. The solution was cooled to room temperature, followed by the addition of 50 mL dichloromethane. The solution was filtered and then washed with a 5% sodium hydroxide aqueous solution. The aqueous layer was then extracted with dichloromethane and the combined organic layers washed with brine (NaCl). The organic phase was dried over anhydrous $Mg_2SO_4$ and concentrated under vacuum to give the crude product. Purification by flash chromatography on silica gel afforded the analytically pure compound (3): $^1$H NMR (300 MHz) (CDCl$_3$): δ 7.35-6.94 (m, 8H), 3.86 (s, 3H).

Example 2

Reaction Step B: Synthesis of
4-hexyl-2-methoxy-1-phenoxybenzene (4a)

Under nitrogen, ZnCl$_2$ (0.5 M solution in tetrahydrofuran; 6.8 mL, 3.41 mmol) was added by syringe to a round-bottomed flask sealed with a rubber septum and purged with nitrogen. Hexyl magnesium chloride (1.0 M solution in THF; 4.0 mL, 4.26 mmol) was then added dropwise by syringe, and the resulting solution was stirred at room temperature for 20 minutes. Next, N-methylpyrrolidinone (4.7 mL) was added by syringe. After 5 minutes, 21.7 mg (0.0426 mmol) Pd(P(t-Bu)$_3$)$_2$ and 500 mg (2.13 mmol) of compound (3) were added. The flask was then fitted with a reflux condenser and heated under refluxed for 48 hours. The flask was then gradually cooled to room temperature, and 20 mL of a 1.0M aqueous HCl solution was added. The resulting mixture was extracted with diethyl ether and the ether extract was washed with water, then dried over anhydrous MgSO$_4$ and concentrated under vacuum to give the crude product. Purification by flash chromatography on silica gel afforded analytically pure compound (4a): $^1$H NMR (300 MHz) (CDCl$_3$): δ 7.36-6.80 (m, 8H), 3.90 (s, 3H), 2.71-2.66 (t, 2H), 1.74-1.67 (m, 2H), 1.42-1.33 (m, 6H), 1.01-0.97 (t, 3H).

Example 3

Reaction Step B: Synthesis of
2-methoxy-4-octyl-1-phenoxybenzene (4b)

The procedure as described above for synthesis of (4a) was used, except that hexyl magnesium chloride was replaced with octyl magnesium chloride. $^1$H NMR (300 MHz) (CDCl$_3$): δ 7.36-6.90 (m, 8H), 3.90 (s, 3H), 2.69-2.65 (t, 2H), 1.72-1.68 (m, 2H), 1.42-1.36 (m, 10H), 1.00-0.94 (t, 3H).

Example 4

Reaction Step C: Synthesis of
5-hexyl-2-phenoxyphenol (5a)

Compound (4a), 1.4 mmol, was dissolved in 3 mL of anhydrous dichloromethane under nitrogen. The temperature of the solution was lowered to −70° C. To the solution of (3) was added 455 mg (1.8 mmol) of boron tribromide (1.8 mL of a 1.0M boron tribromide in dichloromethane solution). The reaction mixture was stirred at −70° C. for one hour, followed by stirring at room temperature for three hours. The reaction progress was monitored by thin layer chromatography. The solution was then quenched with methanol at −70° C. and concentrated. A suspension of the concentrate was washed with 10% aqueous sodium bicarbonate solution. The organic phase was removed, washed with water and then brine (NaCl), dried over anhydrous magnesium sulfate, filtered, and concentrated under vacuum to give the crude product. Purification by flash chromatography on silica gel afforded the analytically pure product (5a): $^1$H NMR (300 MHz) (CDCl$_3$): δ 7.44-6.76 (m, 8H), 5.58 (s, 1H), 2.66-2.61 (t, 2H), 1.71-1.66 (m, 2H), 1.40-1.34 (m, 6H), 1.00-0.95 (t, 3H).

Example 5

Reaction Step C: 5-octyl-2-phenoxyphenol (5b)

The procedure as described above for synthesis of (5a) was used, except that compound (4a) was replaced with compound (4b). $^1$H NMR (300 MHz) (CDCl$_3$) δ 7.43-6.72 (m, 8H), 5.58 (s, 1H), 2.66-2.61 (t, 2H), 1.71-1.66 (m, 2H), 1.39-1.35 (m, 10H), 0.99-0.95 (t, 3H).

Example 6

IC$_{50}$ and MIC$_{99}$ Data For Selected Compounds

| Compound Structure | R | IC$_{50}$ (nM) | MIC$_{99}$ (μM) |
|---|---|---|---|
| OH with phenoxy group, R substituent | —C$_2$H$_5$ | 2000 | 3.75 |
|  | -(n-C$_4$H$_9$) | 80 |  |
|  | -(n-C$_5$H$_{11}$) | 17 | 0.93 |
|  | -(n-C$_6$H$_{13}$) | 10 | 0.93 |
|  | -(n-C$_8$H$_{17}$) | 5 | 0.93 |

Example 7

Experimental Procedure For Obtaining MIC$_{99}$
Results

The Minimum Inhibitory Concentration Experiment (MIC$_{99}$) is the concentration of the growth inhibitor, here a drug analog, that inhibits growth greater than 99%.

A microplate dilution method was used to determine the MIC of the drug analogs capable of inhibiting growth of *Mycobacterium tuberculosis* strain H37Rv in vitro. In a representative experiment, *Mycobacterium tuberculosis* strain H37Rv was cultivated in Middlebrook 7H$_9$Broth containing 10% ADC enrichment and 0.05% Tween-80 to an optical density of 0.2 (600 nm). The *Mycobacterium tuberculosis* culture was then prepared by diluting 1:100 in 7H9 Middlebrook Broth containing 10% ADC enrichment and 0.05% Tween-80.

The drug analogs tested were prepared at 60 μM 5% DMSO in dH$_2$O and diluted 1:2 in Middlebrook 7H$_9$Broth containing 10% ADC enrichment and 0.05% Tween-80 to result in a drug concentration of 30 μM, 100 μl final volumes (Row B, columns 1-12). 50 μl Middlebrook 7H$_9$Broth containing 10% ADC enrichment and 0.05% Tween-80 was added to each remaining well of the 96-well plate (Rows C—H, columns 1-12). A two-fold serial dilution of each drug analog was performed down each column to achieve a concentration range of 30 μM to 0.47 μM, final volume of 50 μl. For example, a dilution series was obtained by removing 50 μl analog-medium mixture from wells in Row B and mixed with the 50 μl of Middlebrook 7H$_9$Broth containing 10% ADC enrichment and 0.05% Tween-80 medium in wells in Row C; mixing and transferring 50 μl of one well with the next consecutive well completes the dilution series. A representative dilution series for a drug plate, listing final drug analog concentrations in each well is shown Table 2 below.

Upon completion of the serial dilutions of each drug analog in Middlebrook $7H_9$Broth containing 10% ADC enrichment and 0.05% Tween-80 medium, 50 μl of the prepared *Mycobacterium tuberculosis* culture was added to each well. The 96-well plates were incubated at 37° C. for 3-5 days. The plate was evaluated for bacterial growth, or non-growth, using an inverted plate reading method. The MIC was determined to be the lowest concentration of drug analog that inhibited visible growth of the bacterial culture.

TABLE 2

Representative dilution series for a drug analog MIC determination plate based on 96-well testing format.

| | Columns 1-12 |
|---|---|
| A | 0 μM |
| B | 30 μM |
| C | 15 μM |
| D | 7.5 μM |
| E | 3.75 μM |
| F | 1.87 μM |
| G | 0.93 μM |
| H | 0.47 μM |

Example 8

Experimental Procedure For Obtaining $IC_{50}$ Results $IC_{50}$ values were determined by measuring the enzyme activity at different inhibitor concentrations. The experimental data were analyzed using Equation 1, where I is the inhibitor concentration and Y is fraction activity.

$$Y=1/(1+[I]/IC50) \quad (1)$$

All experiments were carried out on a CARY-100 Bio (Varian) spectrophotometer at 25° C. The buffer used was 30 mM PIPES, 150 mM NaCl, pH 6.8. Kinetic parameters were determined spectrophotometrically by following the oxidation of NADH to $NAD^+$ at 340 nm ($\epsilon$=6.3 $nM^{-1}$ $cm^{-1}$). Trans-2-dodecenoyl-CoA (DD-CoA) was used as a substrate. Two sets of conditions were used for the $IC_{50}$ determinations.

For inhibitors with $IC_{50}$ values above 0.2 μM, reaction mixtures contained 250 μM NADH, 74 nM InhA, and 25 μM DD-CoA. For inhibitors with $IC_{50}$ values below 0.2 μM, reaction mixtures contained 250 μM NADH, 1 nM InhA, 85 μM DD-CoA, 8% (v/v) glycerol, and 0.1 mg/ml BSA. In each case, the inhibitor concentration was varied over the range of 0-200 μM.

Thus, whereas there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

We claim:

1. A pharmaceutical composition comprising a compound having the formula:

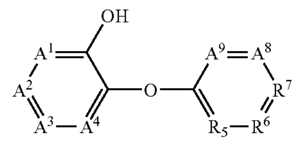

(1)

wherein $A^1$, $A^3$, $A^6$, and $A^8$ independently represent CH or N;

$A^2$ represents N or C—$X^1{}_a$—$R^1$;

$A^4$ represents N or C—$X^2{}_b$—$R^2$;

wherein when $A^3$ is N, then $A^4$ is CH or $CCH_3$, and when $A^4$ is N, then $A^3$ is CH, $R^1$ and $R^2$ independently represent H, or a hydrocarbon containing a minimum of three carbon atoms and a maximum of twenty six carbon atoms for $R^1$, and a minimum of one carbon atom and a maximum of twenty six carbon atoms for $R^2$, wherein the hydrocarbon is unsubstituted, or is substituted with one or more of —OH, —$NH_2$, —SH, halo, or —COOH;

$X^1$ and $X^2$ independently represent —O—, —S—, —NH—, —C(O)O—, —C(O)—, —C(O)NH—, or —$SO_2$NH—;

a and b independently represent 0 or 1, provided that when a and b are both 0, then $R^1$ and $R^2$ are not both H; when a is 1, then $R^1$ is not H; and when b is 1, then $R^2$ is not H;

$A^5$ and $A^9$ independently represent $CR^3$ or N;

$R^3$ represents H, methyl, ethyl, or halo;

$A^7$ represents $CR^4$ or N;

$R^4$ represents H, methyl, ethyl, halo, nitro, amino, amido, or a methyl or ethyl group substituted with halo, nitro, hydroxy, amino, or amido;

provided that $A^2$ and $A^4$ are not both N; and not more than three of $A^5$, $A^6$, $A^7$, $A^8$, and $A^9$ are N, and a pharmaceutically acceptable carrier.

2. The pharmaceutical composition according to claim 1 wherein $A^2$ represents $C(X^1)_a$—$R^1$.

3. The pharmaceutical composition according to claim 2 wherein $A^4$ represents $C(X^2)_b$—$R^2$.

4. The pharmaceutical composition according to claim 3 wherein a and b represent 0.

5. The compound according to claim 4 wherein $R^1$ is H.

6. The pharmaceutical composition according to claim 4 wherein $R^2$ is H.

7. The pharmaceutical composition according to claim 6 wherein $R^1$ is a hydrocarbon containing a minimum of three carbon atoms and a maximum of twenty six carbon atoms.

8. The pharmaceutical composition according to claim 7 wherein the hydrocarbon is alkyl, alkenyl, or alkynyl.

9. The pharmaceutical composition according to claim 8 wherein the hydrocarbon is a straight-chained alkyl group.

10. The pharmaceutical composition according to claim 9 wherein the straight-chained alkyl group contains a maximum of eight carbon atoms.

11. The pharmaceutical composition according to claim 10 wherein the straight-chained alkyl group contains a minimum of four carbon atoms.

12. The pharmaceutical composition according to claim 11 wherein the straight-chained alkyl group is unsubstituted.

13. The pharmaceutical composition according to claim 12 wherein $A^1$ represents CH.

14. The pharmaceutical composition according to claim 13 wherein $A^3$ represents CH.

15. The pharmaceutical composition according to claim 14 wherein $A^5$ represents $CR^3$.

16. The pharmaceutical composition according to claim 15 wherein $R^3$ represents H.

17. The pharmaceutical composition according to claim 16 wherein $A^6$ represents CH.

18. The pharmaceutical composition according to claim 17 wherein $A^7$ represents $CR^4$.

19. The pharmaceutical composition according to claim 18 wherein $R^4$ represents H.

20. The pharmaceutical composition according to claim 19 wherein $A^8$ represents CH.

21. The pharmaceutical composition according to claim 20 wherein $A^9$ represents $CR^3$.

22. The pharmaceutical composition according to claim 21 wherein $R^3$ represents H.

23. The compound according to claim 11 wherein the straight-chained alkyl is substituted with OH.

24. The pharmaceutical composition of claim 1 wherein the compound is represented by the formula

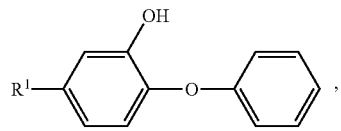

(2)

wherein $R^1$ is a straight-chained alkyl containing a minimum of four carbon atoms and a maximum of twenty six carbon atoms.

* * * * *